United States Patent
Bachand et al.

(10) Patent No.: US 6,340,690 B1
(45) Date of Patent: Jan. 22, 2002

(54) ANTIVIRAL METHODS USING [1,8] NAPHTHYRIDINE DERIVATIVES

(75) Inventors: Benoit Bachand, Montréal; Nghe Nguyen-Ba, Laprairie; Arshad Siddiqui, Dollard des Ormeaux; Sophie Levesque, Mirabel, all of (CA)

(73) Assignee: Bio-Chem Pharma Inc., Quebec (CA)

( * ) Notice: Subject to any disclaimer, the term of this patent is extended or adjusted under 35 U.S.C. 154(b) by 0 days.

(21) Appl. No.: 09/507,936

(22) Filed: Feb. 22, 2000

Related U.S. Application Data

(60) Provisional application No. 60/121,080, filed on Feb. 22, 1999.

(51) Int. Cl.[7] .............................................. A61K 31/435
(52) U.S. Cl. ....................................................... 514/300
(58) Field of Search .......................................... 514/300

(56) References Cited

U.S. PATENT DOCUMENTS

| 4,642,308 | A | * | 2/1987 | Cotrel et al. ................. 514/253 |
| 5,621,010 | A |   | 4/1997 | Sueda et al. ................. 514/596 |

FOREIGN PATENT DOCUMENTS

| EP | 0172083 | 7/1984 |
| EP | 0208621 | 1/1987 |
| EP | 0234971 | 2/1987 |
| EP | 0233801 | 8/1987 |
| EP | 0387582 | 9/1990 |
| EP | 0512899 | 11/1992 |
| FR | 2263752 | 10/1975 |
| WO | 97/34870 | 9/1997 |
| WO | 97/34894 | 9/1997 |

OTHER PUBLICATIONS

Chan, et. al, Bioorganic & Medicinal Chemistry Letters 9 (1999) 2583–2586 "Isoquinoline–LINE–6–Carboxamides as Potent and Selective Anti–Human Cytomegalovirus (HCMV) Inhibitors" Laval.

Self–Replication in a Diels —Alder Reaction, Bing Wang and Ian O. Southerland, Chem. Communications (1997) p. 1495–1496.

Terauchi et al., J. Med Chem 1997, 40, 313–321, "Nicotinamide Derivatives as a New Class of Gastric H+/l+–atpase Inhibitors. 1. Synthesis . . . ".

Xu et al., Journal of Virology, Jul. 1997, p. 5312–5322, vol. 71, No. 7, "Bovine Viral Diarrhea Virus NS3 Serine Proteinase: . . . ".

Zitzmann et al., PNAS, pp 11878–11882, Oct. 12, 1999, vol. 96, No. 21, "Imino Sugars Inhibit the Formation and Secretion of Bovine Viral Diarrhea".

* cited by examiner

*Primary Examiner*—Bernard Dentz
(74) *Attorney, Agent, or Firm*—Arent Fox Kintner Plotkin & Kahn, PLLC

(57) ABSTRACT

The present invention is concerned with novel [1,8] naphthyridine derivatives useful for the inhibition of the hepatitis virus, more specifically the hepatitis C virus.

45 Claims, No Drawings

ANTIVIRAL METHODS USING [1,8] NAPHTHYRIDINE DERIVATIVES

This application claims the benefit of U.S. Provisional Application No. 60/121,080, filed Feb. 22, 1999.

FIELD OF THE INVENTION

The present invention relates to heterocyclic compounds, more specifically derivatives of [1,8] naphthyridine, useful for the inhibition of viral infections.

BACKGROUND OF THE INVENTION

Hepatitis is a disease occurring throughout the world. It is generally or viral nature, although there are other causes known. Viral hepatitis is by far the most common form of hepatitis. Nearly 750,000 Americans are affected by hepatitis each year, and out of those, more than 150,000 are infected with the hepatitis C virus ("HCV").

HCV is a positive-stranded RNA virus belonging to the Flaviviridae family and has closest relationship to the pestiviruses that include hog cholera virus and bovine viral diarrhea virus (BVDV). HCV is believed to replicate through the production of a complementary negative-strand RNA template. Due to the lack of efficient culture replication system for the virus, HCV particles were isolated from pooled human plasma and shown, by electron microscopy, to have a diameter of about 50–60 nm. The HCV genome is a single-stranded, positive-sense RNA of about 9,600 bp coding for a polyprotein of 3009–3030 amino-acids, which is cleaved co and post-translationally by cellular and two viral proteinases into mature viral proteins (core, E1, E2, p7, NS2, NS3, NS4A, NS4B, NS5A, NS5B). It is believed that structural proteins, E1 and E2, the major glycoproteins are embedded into a viral lipid envelope and form stable heterodimers. The structural core protein interacts with the viral RNA genome to form the nucleocapsid. The nonstructural proteins designated NS2 to NS5 code for proteins with enzymatic functions involved in virus replication and protein processing including a polymerase, protease and helicase.

The main sources of contamination with HCV is blood. The magnitude of the HCV infection as a health problem is illustrated by the prevalence among high-risk groups. For example, 60% to 90% of hemophiliacs and more than 80% of intravenous drug abusers in western countries are chronically infected with HCV. For intravenous drug abusers, the prevalence varies from about 28% to 70% depending on the population studied. The proportion of new HCV infections associated with post-transfusion has been markedly reduced lately due to advances in diagnostic tools used to screen blood donors.

The only treatment currently available for HCV infection is interferon-α (IFN-α), either as monotherapy and in combination with ribavirin. However, according to different clinical studies, only 70% of treated patients normalize alanine aminotransferase (ALT) levels in the serum and after discontinuation of IFN, 35% to 45% of these responders relapse. In general, only 40% of patients have long-term responses to IFN/ribavirin combination therapy. On the other hand, pilot studies suggest that combination treatment with IFN plus Ribavirin (RIBA) results in sustained response in the majority of patients. Different genotypes of HCV respond differently to IFN therapy, genotype 1b is more resistant to IFN therapy then type 2 and 3.

In spite of advances in the knowledge of HCV replication and transmission, it therefore appears that to this date, no effective universal treatment of HCV is available. This is due in great part to the fact that only humans and chimpanzees can be infected with the virus. Consequently, there are no in vivo animal models for testing potential therapeutic agents and thus, no vaccine available for hepatitis C. Another factor preventing the development of in vivo assays is that human liver tissue is difficult to obtain and is expensive, thereby preventing its use in large scale screening where large quantities of tissue would be needed. Combined with the prohibitive cost and availability of chimpanzees, in vivo models are presently not amenable for screening purposes.

Jin et al. described [1,6] naphthyridine derivatives useful as inhibitors of human cytomegalovirus (HCMV). A [1,8] naphthyridine derivative was also identified as having such inhibiting activity, though to lesser extent, i.e. [1,8] naphthyridine-2-carboxylic acid 2-methoxybenzyl-amine. However, no other use is suggested for this particular compound. There is therefore a great need for the development of a hepatitis virus inhibitor, and particularly HCV.

The herpes group of viruses which includes Epstein-Barr virus (EBV), Varicella Zoster virus (VZV), Herpes Simplex viruses (HSV-1, HSV-2) and Human Herpes virus (HHV6) is recognized as an important pathogen in patients with AIDS. These viruses often contribute to the immunosuppression observed in such patients and may cause disseminated disease involving the lungs, gastrointestinal tract, central nervous system, or eyes.

All human Herpes viruses have a worldwide distribution and are amongst the most difficult human pathogens to control. Currently, considerable efforts are being directed towards the development of vaccines and antiviral agents that will be active against Herpes viruses, particularly Herpes Simplex viruses HSV-1 and HSV-2, and Varicella Zoster virus (VZV). A number of nucleosides and nucleotides derivatives are active against primary and recurrent HSV infection; of these, acyclovir is the most used drug. However, among patients with AIDS, acyclovir-resistant HSV-2 may lead to chronic progressive infections.

There is therefore a need for development of potent and non-toxic agents against Herpes viruses and hepatitis viruses.

SUMMARY OF THE INVENTION

In accordance with the present invention, there is provided a method for the inhibition of a viral infection in a mammal, the method comprising administering to the mammal an antiviral amount of a [1,8] naphthyridine derivative of Formula I or a pharmaceutically acceptable salt thereof;

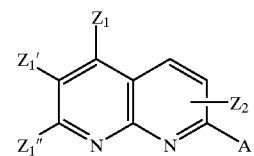

(I)

wherein $Z_1$, $Z'_1$, $Z''_1$, and $Z_2$ are independently H, halogen, carboxyl, amino, amidino, guanidino, nitro, OH, SH, CN, $C_{1-6}$ alkyl, $C_{2-6}$ alkenyl, $C_{2-6}$ alkynyl, $C_{1-6}$ alkoxy or $C_{1-6}$ heteroalkyl;

A is

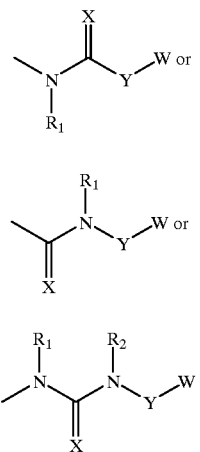

X is O, NH, or S;
Y is O, S, $(CH_2)_n$, $O(CH_2)_n$, or $S(CH_2)_n$; with n is 0 to 6;
$R_1$ and $R_2$ are independently H or $C_{1-6}$ alkyl, $C_{2-6}$ alkenyl, $C_{2-6}$ alkynyl; or $R_1$ and $R_2$ together form a saturated or unsaturated 5 or 6 member heterocycle; and
W is $C_{6-12}$ aryl, $C_{6-12}$ heteroaryl, or $C_{3-12}$ heterocycle In accordance with the present invention, there is also provided a [1,8] naphthyridine derivative of Formula I or pharmaceutically acceptable salts thereof;

(I)

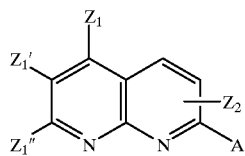

wherein;
A, $Z_1$, $Z'_1$, $Z''_1$, and $Z_2$ are as defined above; with the provisos that:
1) when; Y is $CH_2$, X is O, $R_1$, $Z_1$, $Z_1'$, $Z_1''$ and $Z_2$ are H, and A is

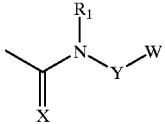

then W is not 2-methoxyphenyl or 3-trifluoromethylphenyl; and
2) when Y is $(CH_2)_0$, X is O, $R_1$, $Z_1$, $Z_1'$, $Z_1''$ and $Z_2$ are H, and A is

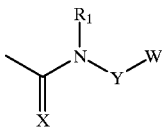

then W is not phenyl, 3-trifluoromethylphenyl or 3-pyridinyl.

DETAILED DESCRIPTION OF THE INVENTION

As used in this application, the term "alkyl" represents an unsubstituted or substituted (by a halogen, nitro, aminoamidino, amidino, guanido, $CONH_2$, COOH, O—$C_{1-6}$ alkyl, O—$C_{2-6}$alkenyl, O—$C_{2-6}$ alkynyl, amino, hydroxyl or COOQ, wherein Q is $C_{1-6}$ alkyl, $C_{2-6}$ alkenyl, a $C_{2-6}$ alkynyl) straight chain, branched chain, or cyclic hydrocarbon moiety (e.g. isopropyl, ethyl, flurohexyl or cyclopropyl). The term alkyl is also meant to include alkyls in which one or more hydrogen atoms is replaced by an halogen, more preferably, the halogen is fluoro (e.g., $CF_3$—, or $CF_3CH_2$—).

The terms "alkenyl" and "alkynyl" represent an alkyl containing at least one unsaturated group (e.g., allyl).

The term "heteroalkyl" represents an alkyl, alkenyl, or alkynyl in which a C atom which is part of the straight chain, branched chain or cyclic hydrocarbon moiety is replaced by one or more heteroatom such as oxygen, sulfur and nitrogen (e.g., ether, thiohexanoyl, thiomorpholino, isothiazole, imidazole, triazole, ethylmethylsulfone or ethylthio).

The term "heterocycle" represents a cyclic heteroalkyl (imidazole, isothiazole, or triazole)

The term "aryl" represents a carbocyclic moiety which may be substituted (by a $C_{1-6}$ alkyl, $C_{2-6}$alkenyl, a $C_{2-6}$alkynyl, halogen, nitro, aminoamidino, amidino, guanido, $CONH_2$, COOH, O—$C_{1-6}$ alkyl, O—$C_{2-6}$ alkenyl, O—$C_{2-6}$ alkynyl, amino, hydroxyl or COOQ, wherein Q is $C_{1-6}$ alkyl, $C_{2-6}$ alkenyl, a $C_{2-6}$ alkynyl) and containing at least one benzenoid-type ring (e.g., phenyl and naphthyl).

The term "aralkyl" represents an aryl group attached to the adjacent atom by a $C_{1-6}$alkyl, $C_{1-6}$alkenyl, or $C_{1-6}$alkynyl (e.g., benzyl).

The term "aryloxy" represents an aryl or aralkyl moiety covalently bonded through an oxygen atom (e.g., phenoxy).

The term "heteroaryl" represents an aryl, aryloxy, or aralkyl in which a C atom which is a member of the carbocyclic moeity is replaced by at least one heteroatom (e.g., N, or S) (e.g pyridine, isoquinoline, or benzothiophene).

The term "acyl" refers to a radical derived from a carboxylic acid, substituted (by halogen (F, Cl, Br, I), $C_{6-20}$ aryl or $C_{1-6}$ alkyl) or unsubstituted, by replacement of the —OH group. Like the acid to which it is related, an acyl radical may be aliphatic or aromatic, substituted (by halogen, $C_{1-5}$ alkoxyalkyl, nitro or OH) or unsubstituted, and whatever the structure of the rest of the molecule may be, the properties of the functional group remain essentially the same (e.g., acetyl, propionyl, isobutanoyl, pivaloyl, hexanoyl, trifluoroacetyl, chloroacetyl, and cyclohexanoyl).

Preferred compounds of the present invention comprise those wherein the following embodiments are present, either independently or in combination:

Preferably, $Z_1$, $Z_1'$, $Z_1''$ and $Z_2$ are independently $C_{1-6}$ alkyl, $C_{2-6}$ alkenyl, $C_{2-6}$ alkynyl which can be substituted with one or more halogen, OH, carboxy, amino, guanidino, amidino, nitro, SH or CN.

More preferably, $Z_1$, $Z_1'$, $Z_1''$ are independently $C_{1-6}$ alkyl, OH, halogen or H.

More preferably, $Z_1$, $Z_1'$, $Z_1''$ are independently methyl, ethyl, OH, halogen or H.

More preferably, at least one of $Z_1$, $Z_1'$, $Z_1''$ is H.

More preferably, at least two of $Z_1$, $Z_1'$, $Z_1''$ are H. $Z_1$, $Z_1'$, $Z_1''$ are most preferably H.

More preferably, $Z_2$ is $C_{1-6}$ alkyl, OH, halogen, or H.

More preferably, $Z_2$ is methyl, ethyl, OH, halogen, or H. $Z_2$ is most preferably H.

Preferably, $R_1$ and $R_2$ are independently $C_{1-6}$ alkyl, $C_{2-6}$ alkenyl, $C_{1-6}$ alkynyl which is substituted by one or more $C_{1-6}$ alkyl, $C_{1-6}$ alkoxy or $C_{1-6}$ heteroalkyl, halogen, amino, guanidino, amidino, nitro, OH, SH or CN.

Preferably, $R_1$ and $R_2$ together form a saturated or unsaturated 5 or 6 member heterocycle substituted with one or more $C_{1-6}$ alkyl, $C_{2-6}$ alkenyl, $C_{2-6}$ alkynyl, $C_{1-6}$ alkoxy or $C_{1-6}$ heteroalkyl, halogen, amino, guanidino, amidino, nitro, OH, SH or CN.

More preferably, $R_1$ is $C_{1-6}$ alkyl or H.

More preferably, $R_1$ is methyl, ethyl or H. $R_1$ is most preferably H.

More preferably, $R_2$ is $C_{1-6}$ alkyl or H.

More preferably, $R_2$ is methyl, ethyl or H. $R_2$ is most preferably H.

Preferably, W is $C_{6-12}$ aryl, $C_{6-12}$ heteroaryl, $C_{3-12}$ heterocycle, either of which is substituted with one or more $C_{1-6}$ alkyl, $C_{2-6}$ alkenyl, $C_{2-6}$ alkynyl, $C_{1-6}$ perfluoroalkyl, $C_{1-6}$ alkoxy, $C_{1-6}$ perfluoroalkoxy, $C_{1-6}$ heteroalkyl, $C_{1-6}$ perfluoroalkylthio, halogen, amino, guanidino, amidino, nitro, OH, COOH, SH or CN.

Preferably, W is $C_{6-12}$ aryl, $C_{6-12}$ heteroaryl, $C_{3-12}$ heterocycle, either of which is substituted with one or more $C_{1-6}$ alkyl, $C_{2-6}$ alkenyl, $C_{2-6}$ alkynyl, $C_{1-6}$ perfluoroalkyl, $C_{1-6}$ alkoxy, $C_{1-6}$ perfluoroalkoxy, $C_{1-6}$ heteroalkyl, $C_{1-6}$ perfluoroalkylthio, OH, COOH, SH or CN. W is more preferably phenyl or pyridinyl unsubstituted or substituted with one or more $C_{1-6}$ alkoxy group. W is most preferably phenyl or pyridinyl unsubstituted or substituted with one or more —O-methyl or O-ethyl.

Y is preferably $(CH_2)_n$ and wherein n is chosen between 0 to 6.

Y is preferably $(CH_2)_n$ and wherein n is chosen between 1 to 4.

Y is preferably $(CH_2)_n$ and wherein n is 1.

X is preferably O.

X is preferably S.

X is preferably NH.

A is preferably

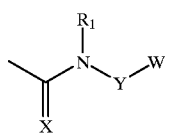

A is preferably

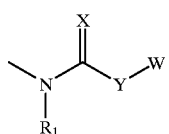

A is preferably

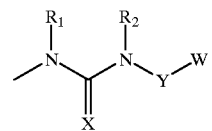

Y is preferably $(CH_2)_n$ and n is 0.
Y is more preferably $(CH_2)_n$ and n is 1.
Y is most preferably $(CH_2)_n$ and n is 2.
$Z_1$, $Z_1'$, $Z_1''$ and $Z_2$ are preferably H.
$R_1$, $Z_1$, $Z_1'$, $Z_1''$ and $Z_2$ are preferably H.

In an alternative embodiment, $R_1$, $Z_1$, $Z_1'$, $Z_1''$ and $Z_2$ are H and Y is $(CH_2)_n$ wherein n is chosen between 0 to 6. n is preferably 0.

In an alternative embodiment, X is O, $R_1$ is H, $Z_1$, $Z_1'$, $Z_1''$ are H and $Z_2$ is H.

In an alternative embodiment X is S, $R_1$ is H, $Z_1$, $Z_1'$, $Z_1''$ are H and $Z_2$ is H.

In an alternative embodiment X is NH, $R_1$ is H, $Z_1$, $Z_1'$, $Z_1''$ are H and $Z_2$ is H.

In a more preferred embodiment, the compounds of the present invention are represented by formula (Ia)

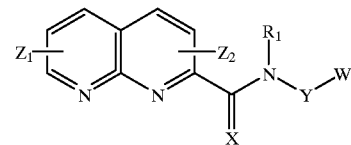

(Ia)

wherein;
X is O or NH and each of $Z_1$, $Z_2$, $R_1$, , Y and W are as defined above.

More preferably, the compounds of the present invention are represented by formula (Ib)

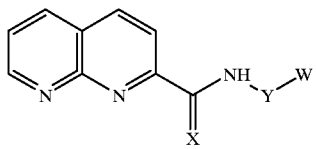

(Ib)

wherein;
X is O or NH and each of Y and W are as defined above
Preferably, the [1,8] naphthyridine derivative is in the form of the (+) enantiomer, the (−) enantiomer or mixture of the (+) and (−) enantiomer including racemic mixture.

Preferably, the [1,8] naphthyridine derivative is in the form of the (+) enantiomer at least 95% free of the corresponding (−) enantiomer.

More Preferably, the [1,8] naphthyridine derivative is in the form of the (+) enantiomer at least 97% free of the corresponding (−) enantiomer.

Most Preferably, the [1,8] naphthyridine derivative is in the form of the (+) enantiomer at least 99% free of the corresponding (−) enantiomer.

Preferably, the [1,8] naphthyridine derivative is in the form of the (−) enantiomer at least 95% free of the corresponding (+) enantiomer.

More Preferably, the [1,8] naphthyridine derivative is in the form of the (−) enantiomer at least 97% free of the corresponding (+) enantiomer.

Preferably, the [1,8] naphthyridine derivative is in the form of the (−) enantiomer at least 99% free of the corresponding (+) enantiomer.

In one embodiment, the viral infection is chosen from Flavivirus infections.

In one embodiment, the Flavivirus infection is chosen from Hepatitis C (HCV), bovine diarrhea (BVDV), hog cholera and yellow fever.

In an other embodiment, the Flavivirus infection is Hepatitis C.

In an other embodiment, the present invention also provides a method for identifying compounds with anti-Flaviviral activity which comprises the step of screening the compounds in a BVDV assay and selecting compounds which show anti-BVDV activity.

In an other embodiment, the present invention also provides a method for identifying compounds with anti-HCV activity which comprises the step of screening the compounds in a BVDV assay and selecting compounds which show anti-BVDV activity.

Preferably the viral infection is hepatitis or herpes.
More preferably, the viral infection is HBV or HCV.
Most preferably, the viral infection is HCV
Alternatively, the viral infection is HSV-1 or HSV-2.

In a preferred embodiment, the [1,8] naphthyridine derivative is selected from the group consisting of:
[1,8] naphthyridine-2-carboxylic acid 2-methoxybenzylamide (Compound#1);
[1,8] naphthyridine-2-carboxylic acid benzylamide (Compound#2);
[1,8] naphthyridine-2-carboxylic acid 4-methoxybenzylamide (Compound#3);
[1,8] naphthyridine-2-carboxylic acid 3-methoxybenzylamide (Compound#4);
[1,8] naphthyridine-2-carboxylic acid 2,4,6-trimethoxybenzylamide (Compound#5);
[1,8] naphthyridine-2-carboxylic acid 2,3-dimethoxybenzylamide (Compound#6);
[1,8] naphthyridine-2-carboxylic acid 2,4-dimethoxybenzylamide (Compound#7);
[1,8] naphthyridine-2-carboxylic acid 2-isopropoxybenzylamide (Compound#8);
(+)-[1,8] naphthyridine-2-carboxylic acid 2-sec-butoxybenzylamide (Compound#9);
(−)-[1,8] naphthyridine-2-carboxylic acid 2-sec-butoxybenzylamide (Compound#10);
[1,8] naphthyridine-2-carboxylic acid [2-(2-methoxyphenyl)ethyl]amide (Compound#11);
[1,8] naphthyridine-2-carboxylic acid (pyridin-3-ylmethyl)amide (Compound#12);
[1,8] naphthyridine-2-carboxylic acid (pyridin-2-ylmethyl)amide (Compound#13);
[1,8] naphthyridine-2-carboxylic acid pyridin-4-ylamide (Compound#14);
[1,8] naphthyridine-2-carboxylic acid pyridin-2-ylamide (Compound#15);
[1,8] naphthyridine-2-carboxylic acid 2-fluorobenzylamide (Compound#16);
[1,8] naphthyridine-2-carboxylic acid 2-chlorobenzylamide (Compound#17);
[1,8] naphthyridine-2-carboxylic acid 2-trifluoromethoxybenzylamide (Compound#18);
[1,8] naphthyridine-2-carboxylic acid (3-nitrophenyl)amide (Compound#19);
N-(5,7-dimethyl-[1,8] naphthyridin-2-yl)-2-(2-methoxyphenyl)acetamide (Compound#20);
[1,8] naphthyridine-2-carboxylic acid benzyloxyamide (Compound#21);
[1,8] naphthyridine-2-carboxylic acid thiazol-2-ylamide (Compound#22);
[1,8] naphthyridine-2-carboxylic acid benzothiazol-2-ylamide (Compound#23);
[1,8] naphthyridine-2-carboxylic acid (2-fluoro-phenyl)amide (Compound#24);
[1,8] naphthyridine-2-carboxylic acid 2-methoxy-benzyl) methylamide (Compound#25);
[1,8] naphthyridine-2-carbothioic acid 2-methoxybenzylamide (Compound#26);
(2-methoxy-benzyl)-[1,8]naphthyridine-2-carboxamidine trifluoroacetate (Compound#27);
[1,8] naphthyridine-2-carboxylic acid phenyl-amide (Compound#28);
[1,8] naphthyridine-2-carboxylic acid pyridin-3-yl-amide (Compound #29);
[1,8] naphthyridine-2-carboxylic acid (phenyl-3-trifluoromethyl)amide (Compound#30); and
[1,8] naphthyridine-2-carboxylic acid (phenylmethyl-3-trifluoromethyl)-amide (Compound#31).

More preferably, the [1,8] naphthyridine derivative is selected from the group consisting of:
[1,8] naphthyridine-2-carboxylic acid 2-methoxybenzylamide (Compound#1);
[1,8] naphthyridine-2-carboxylic acid benzylamide (Compound#2);
[1,8] naphthyridine-2-carboxylic acid 4-methoxybenzylamide (Compound#3);
[1,8] naphthyridine-2-carboxylic acid 3-methoxybenzylamide (Compound#4);
[1,8] naphthyridine-2-carboxylic acid 2,4,6-trimethoxybenzylamide (Compound#5);
[1,8] naphthyridine-2-carboxylic acid (pyridin-3-ylmethyl)-amide (Compound#12);
[1,8] naphthyridine-2-carboxylic acid 2-fluoro-benzylamide (Compound#16); and
[1,8] naphthyridine-2-carboxylic acid 2-chloro-benzylamide (Compound#17).

In accordance with the present invention there is provided a composition useful as an antiviral agent, the composition comprising at least one [1,8] naphthyridine derivative of Formula I, Ia, or Ib or a pharmaceutically acceptable salt thereof in combination with a pharmaceuticcaly acceptable carrier.

Preferably, the antiviral activity of the composition of the present invention is anti-hepatitis or anti-herpes.

More preferably, the antiviral activity of the composition of the present invention is anti-hepatitis activity is anti-HBV or anti-HCV.

Most preferably, the antiviral activity of the composition of the present invention is anti-HCV.

Alternatively, the antiviral activity of the composition of the present invention is anti-HSV-1 or anti-HSV-2.

In accordance with the present invention, there is also provided a [1,8] naphthyridine derivative of Formula (I) (Ia) or (Ib) or pharmaceutically acceptable salts thereof; with the provisos that:

1) when; Y is $CH_2$, X is O, $R_1$, $Z_1$, $Z_1'$, $Z_1''$ and $Z_2$ are H, and A is

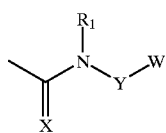

when W is not 2-methoxyphenyl or 3-trifluoromethylphenyl; and 2) when; Y is $(CH_2)_0$, X is O, $R_1$, $Z_1$, $Z_1'$, $Z_1''$ and $Z_2$ are H, and A is

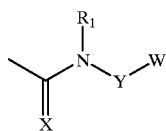

then W is not phenyl, 3-trifluoromethylphenyl or 3-pyridinyl.

Compounds of the present invention can be synthesized using conventional preparative steps and recovery methods known to those skilled in the art of organic chemistry. Examples of such syntheses are provided in the experimental section.

The preferred general synthetic approach for the present [1,8] naphthyridine derivatives, as shown in the examples, comprises reacting [1,8] naphthyridine-2-carboxylic acid, which is commercially available, with a selected amino compound to form the [1,8] naphthyridine derivative of the present invention. Other modifications can be made to the resulting molecule in accordance with well known procedures in the field of organic synthesis.

Those skilled in the art will appreciate that certain compounds of the present invention may contain one or more chiral centers and thus exists in the form of many different isomers, i.e., enantiomers, diastereoisomers and epimers. All such enantiomers, diastereoisomers and epimers are within the scope of the present invention, either in pure form or in admixture, including racemic mixtures.

Certain [1,8] naphthyridine derivatives of the present invention form pharmaceutically acceptable salts. For example, compounds with basic substituents such as an amino group form salts with weaker acids. Examples of suitable acids for salt formation include hydrochloric, sulfuric, phosphoric, acetic, citric, oxalic, malonic, salicylic, malic, fumaric, succinic, ascorbic, maleic, methanesulfonic, trifluoroacetic and other mineral and carboxylic acids well known to those skilled in the art. The salts are prepared by contacting the free base form with a sufficient amount of the desired acid to produce a salt in a conventional manner. The free base forms may be regenerated by treating the salt with a suitable diluted aqueous base solution such as dilute aqueous sodium hydroxide, potassium carbonate, ammonia and sodium bicarbonate. The free base forms may differ from their respective salt forms somewhat in certain physical properties, such as solubility in polar solvents, but the acid and base salts are otherwise equivalent to their respective free base forms for purposes of the present invention.

The present invention is also concerned with a composition for inhibiting the hepatitis C virus. The composition comprises an effective amount of a compound of Formula I wherein A, W, X, Y, $Z_1$, $Z_1'$, $Z_1''$, $Z_2$, n, and $R_1$–$R_3$ are as defined above without the proviso, in association with a pharmaceutically acceptable carrier. Typically, they contain from about 0.1% to about 99% by weight of active compound, and preferably from about 10% to about 60% by weight depending on which method of administration is employed. The compositions may be in the form of tablets, capsules, caplets, powders, granules, lozenges, suppositories, reconstitutable powders or liquid preparations such as oral or sterile parenteral solutions or suspensions. Conventional carriers include binding agents such as acacia, gelatin, sorbitol, polyvinylpyrrolidone; fillers such as lactose, sugar, maize-starch, calcium phosphate, sorbitol or glycine; disintegrants such as starch, polyvinylpyrrolidone, sodium starch glycollate or microcrystalline cellulose; or pharmaceutically acceptable wetting agent such as sodium lauryl sulphate.

The present compounds may be injected parenterally, i.e., intramuscularly, intravenously, or subcutaneously. For parenteral administration, the compound may be used in the form of sterile solutions containing other solutes, for example, sufficient saline or glucose to make the solution isotonic.

The compounds may be administered orally in the form of tablets, capsules, or granules containing suitable conventional carriers or excipients such as starch, lactose, white sugar etc. The compounds may be administered orally in the form of solutions that may contain coloring and/or flavoring agents. The compounds may also be administered sublingually in the form of tracheas or lozenges in which each active ingredient is mixed with sugar or corn syrups, flavoring agents and dyes, and then dehydrated sufficiently to make the mixture suitable for pressing into solid form. The amount of active ingredient administered orally will depend on bioavailability of the specific compound.

The solid oral compositions may be prepared by conventional methods of blending, filling, tableting etc. Repeated blending operations may be used to distribute the active agent throughout those compositions employing large quantities of fillers. Such operations are conventional in the art. The tablets may be coated according to methods well known in normal pharmaceutical practice, in particular with an enteric coating.

Oral liquid preparations may be in the form of emulsions, syrups, or elixirs, or may be presented as a dry product for reconstitution with water or other suitable vehicle before use. Such liquid preparations may or may not contain conventional additives. For example, suspending agents, such as sorbitol, syrup, methyl cellulose, gelatin, hydroxyethylcellulose, carboxymethylcellulose, aluminum stearate gel, or hydrogenated edible fats; emulsifying agents, such as sorbitan monooleate or acacia; non-aqueous vehicles (which may include edible oils), such as almond oil, fractionated coconut oil, oily esters selected from the group consisting of glycerin, propylene glycol, ethylene glycol, and ethyl alcohol; preservatives, for instance methyl para-hydroxybenzoate, ethyl para-hydroxybenzoate, n-propyl para-hydroxybenzoate, or n-butyl para-hydroxybenzoate of sorbic acid; and, if desired, conventional flavoring or coloring agents.

For parenteral administration, fluid unit dosage forms may be prepared by utilizing the compound and a sterile vehicle, and, depending on the concentration employed, may be either suspended or dissolved in the vehicle. Once in solution, the compound may be injected and filter sterilized before filling a suitable vial or ampoule and subsequently sealing the carrier or storage package. Adjuvants, such as a local anesthetic, a preservative or a buffering agent, may be dissolved in the vehicle prior to use. Stability of the pharmaceutical composition may be enhanced by freezing the composition after filling the vial and removing the water under vacuum, (e.g., freeze-drying the composition). Parenteral suspensions may be prepared in substantially the same manner, except that the peptide should be suspended in the vehicle rather than being dissolved, and, further, sterilization is not achievable by filtration. The compound may be sterilized, however, by exposing it to ethylene oxide before suspending it in the sterile vehicle. A surfactant or wetting solution may be advantageously included in the composition to facilitate uniform distribution of the compound.

An inhibiting amount can be defined as the amount of active compound required to slow the progression of viral replication or reduce viral load from that which would otherwise occur without administration of the compound. Or, it is an amount of active compound required to slow the progression or reduce the intensity of symptoms resulting from hepatitis C virus or elimination thereof.

The compounds of the invention may also be used in combination with other antiviral agents.

In one embodiment, the compounds of the invention may be employed together with or at least one other antiviral agent chosen from protease inhibitors, polymerase inhibitors, and helicase inhibitors.

In one embodiment, the compounds of the invention may be employed together with at least one other antiviral agent chosen from Interferon and Ribavirin.

In one embodiment, the compounds of the invention may be employed together with at least one other antiviral agent chosen from Interferon-α and Ribavirin.

The combinations referred to above may conveniently be presented for use in the form of a pharmaceutical formulation and thus pharmaceutical formulations comprising a combination as defined above together with a pharmaceutically acceptable carrier therefor comprise a further aspect of the invention.

The individual components of such combinations may be administered either sequentially or simultaneously in separate or combined pharmaceutical formulations.

When the compound (I) or a pharmaceutically acceptable salts thereof is used in combination with a second therapeutic agent active against the same virus the dose of each compound may be either the same as or differ from that when the compound is used alone. Appropriate doses will be readily appreciated by those skilled in the art.

Physicians will determine the dosage of the present therapeutic agents that will be most suitable. Dosages may vary with the mode of administration and the particular compound chosen. In addition, the dosage may vary with the particular patient under treatment. The dosage of the compound used in the treatment will vary, depending on viral load, the weight of the patient, the relative efficacy of the compound and the judgment of the treating physician. Such therapy may extend for several weeks or months, in an intermittent or uninterrupted manner.

The following examples are provided to illustrate various embodiments of the present invention and shall not be consider as limiting its scope.

EXAMPLE 1

[1,8] naphthyridine-2-carboxylic acid 2-methoxybenzylamide (Compound#1)

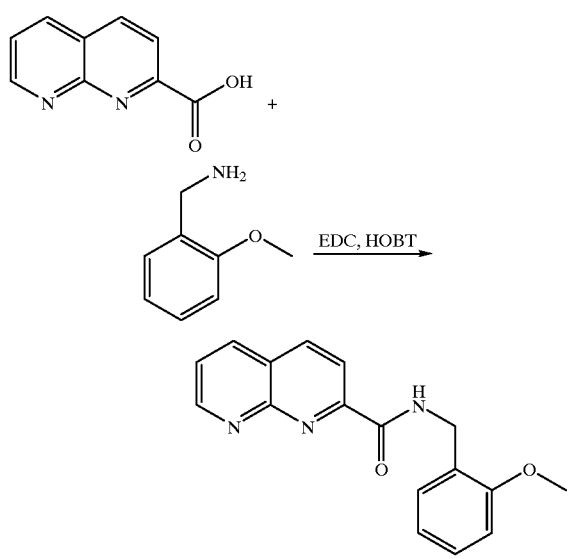

1-(3-dimethylaminopropyl)-3-ethylcarbodiimide hydrochloride (EDC) (132 mg, 0.69 mmol, 1.1 eq.) was added to a solution of the acid (111 mg, 0.63 mmol), the amine (123 μL, 0.95 mmol, 1.5 eq.) and hydroxybenzotriazole (HOBT) (93 mg, 0.69 mmol, 1.1 eq.) in dry DMF (5 mL) at room temperature. Reaction mixture was stirred at room temperature for 18 hours. It was then poured into brine, extracted with ethyl acetate (3 times). Combined organic extracts were washed with citric acid 10%, sodium bicarbonate saturated solution, brine, dried over magnesium sulfate and concentrated to give a white solid (78% yield). when purification is needed, it was done by flash chromatography using ethylacetate as the eluent. $^1$H NMR (300 MHz; CDCl$_3$): 9.15 (m, 1H); 8.68 (bs, 1H); 8.45 (d, 1H, J=8.5 Hz); 8.34 (d, 1H, J=8.5 Hz); 8.25 (dd, 1H, J=1.9 and 8.2 Hz); 7.54 (dd, 1H, J=4.4 and 8.1 Hz); 7.37 (dd, 1H, J=1.6 and 7.4 Hz); 7.27–7.22 (m, 1H); 6.88 (m, 2H); 4.70 (d, 2H, J=6.3 Hz) and 3.86 (s, 3H) ppm.

Based on a method similar to that of example 1, the following compounds were prepared:

EXAMPLE 2

[1,8] naphthyridine-2-carboxylic acid benzylamide Compound#2

$^1$H NMR (300 MHz; CDCl$_3$): 9.15 (m, 1H); 8.70 (br.m, 1H); 8.49 (d, 1H, J=8.2 Hz); 8.38 (d, 1H, J=8.4 Hz); 8.28 (m, 1H); 7.57 (m, 1H); 7.30–7.10 (br. m, 5H) and 4.74 (d, 2H, J=6.1 Hz) ppm.

EXAMPLE 3

[1,8] naphthyridine-2-carboxylic acid 4-methoxybenzylamide Compound#3

$^1$H NMR (300 MHz; CDCl$_3$): 9.13 (m, 1H); 8.65 (bs, 1H); 8.44 (d, 1H, J=8.2 Hz); 8.35 (d, 1H, J=8.5 Hz); 8.25 (dd, 1H, J=1.9 and 8.2 Hz); 7.54 (dd, 1H, J=4.1 and 8.1 Hz); 7.29 (d, 2H, J=8.5 Hz); 6.13 (d, 2H, J=8.5 Hz); 4.61 (d, 2H, J=6 Hz) and 3.75 (s, 3H) ppm.

EXAMPLE 4

[1,8] naphthyridine-2-carboxylic acid 3-methoxy-benzylamide Compound#4

$^1$H NMR (400 MHz; CDCl$_3$): 9.10 (dd, 1H, J=1.9 and 4.1 Hz); 8.66 (bs, 1H); 8.41 (d, 1H, J=8.3 Hz); 8.32 (d, 1H, J=8.3 Hz); 8.22 (dd, 1H, J=1.9 and 8.1 Hz); 7.52 (dd, 1H, J=4.2 and 8.2 Hz); 7.18 (t, 1H, J=8.0 Hz); 6.90 (d, 1H, J=7.6 Hz); 6.85 (d, 1H, J=1.9 Hz); 6.75 (dd, 1H, J=2.4 and 8.2 Hz); 4.61 (d, 2H, J=6.1 Hz) and 3.72 (s, 3H) ppm.

EXAMPLE 5

[1,8] naphthyridine-2-carboxylic acid 2,4,6-trimethoxy-benzylamide Compound#5

$^1$H NMR (300 MHz; CDCl$_3$): 9.14 (dd, 1H, J=1.9 and 4.1 Hz); 8.49 (d, 1H, J=8.2 Hz); 8.36–8.33 (m, 2H); 8.26 (dd, 1H, J=1.9 and 8.2 Hz); 7.54 (dd, 1H, J=4.1 and 8.2 Hz); 6.13 (s, 2H); 4.71 (d, 2H, J=5.2 Hz) and 3.82 (s, 9H) ppm.

EXAMPLE 6

[1,8] naphthyridine-2-carboxylic acid 2,3-dimethoxy-benzylamide Compound#6

$^1$H NMR (300 MHz; CDCl$_3$): 9.14 (dd, 1H, J=1.9 and 4.3 Hz); 8.67 (bs, 1H); 8.44 (d, 1H, J=8.2 Hz); 8.35 (d, 1H, J=8.5 Hz); 8.25 (dd, 1H, J=1.9 and 8.1 Hz); 7.54 (dd, 1H, J=4.1 and 8.2 Hz); 7.03–6.97 (m, 2H); 6.86–6.83 (m, 1H); 4.73 (d, 2H, J=6 Hz); 3.89 (s, 3H) and 3.84 (s, 3H) ppm.

EXAMPLE 7

[1,8] naphthyridine-2-carboxylic acid 2,4-dimethoxy-benzylamide Compound#7

$^1$H NMR (300 MHz; CDCl$_3$): 9.12 (bs, 1H); 8.60 (bs, 1H); 8.41 (d, 1H, J=8.2 Hz); 8.31 (d, 1H, J=8.5 Hz); 8.22 (dd, 1H, J=1.9 and 8.2 Hz); 7.52 (dd, 1H, J=4.1 and 8.2 Hz); 7.27 (d, 1H, J=6 Hz); 6.42–6.38 (m, 2H); 4.60 (d, 2H, J=6 Hz); 3.81 (s, 3H) and 3.75 (s, 3H) ppm.

EXAMPLE 8

[1,8] naphthyridine-2-carboxylic acid 2-isopropoxy-benzylamide Compound#8

$^1$H NMR (300 MHz; CDCl$_3$): 9.17 (m, 1H); 8.72 (br. M, 1H); 8.49 (d, 1H, J=8.5 Hz); 8.38 (d, 1H, J=8.2 Hz); 8.27 (m, 1H); 7.57 (dd, 1H, J=4.1 and 9.1 Hz); 7.35 (m, 1H); 7.30–7.20 (m, 1H, mixed with CDCl$_3$); 6.88 (m, 2H); 4.72 (d, 2H, J=6 Hz); 4.62 (m, 1H); 1.40 (s, 3H) and 1.38 (s, 3H) ppm.

EXAMPLE 9

(+)-[1,8] naphthyridine-2-carboxylic acid 2-sec-butoxy-benzylamide Compound#9

α$_D$: +17.1° (MeOH, 22.7 mM, room temp.) $^1$H NMR (300 MHz; CDCl$_3$): 9.17 (m, 1H); 8.69 (br. m, 1H); 8.48 (d, 1H, J=8.2 Hz); 8.38 (d, 1H, J=8.28 Hz); 8.28 (dd, 1H, J=1.9 and 8.2 Hz); 7.58 (m, 1H); 7.36 (d, 1H, J=7.7 Hz); 7.23 (d, 1H, under CDCl$_3$); 6.88 (m, 2H); 4.73 (d, 2H, J=6.0 Hz); 4.40 (m, 1H); 1.77 (m, 2H); 1.33 (d, 3H, J=6.1 Hz) and 0.97 (t, 3H, J=7.4 Hz) ppm.

EXAMPLE 10

(−)-[1,8] naphthyridine-2-carboxylic acid 2-sec-butoxy-benzylamide Compound#10

α$_D$: −21.1° (MeOH, 24.6 mM, room temp.) $^1$H NMR (300 MHz; CDCl$_3$): 9.13 (m, 1H); 8.68 (b. m, 1H); 8.44 (d, 1H, J=8.5 Hz); 8.33 (d, 1H, J=8.5 Hz); 8.23 (dd, 1H, J=1.9 and 8.2 Hz); 7.52 (m, 1H); 7.35 (m, 1H); 7.20 (m, 1H); 6.86 (m, 2H); 4.71 (d, 2H, J=6.0 Hz); 4.37 (m, 1H); 1.72 (m, 2H); 1.30 (d, 3H, J=6.0 Hz) and 0.95 (t, 3H, J=7.4 Hz) ppm.

EXAMPLE 11

[1,8] naphthyridine-2-carboxylic acid [2-(2-methoxy-phenyl)-ethyl]-amide Compound#11

$^1$H NMR (300 MHz; CDCl$_3$): 9.14 (bs, 1H); 8.60 (m, 1H); 8.42 (d, 1H, J=8.2 Hz); 8.34 (d, 1H, J=8.5 Hz); 8.24 (dd, 1H, J=1.9 and 8.2 Hz); 7.54 (dd, 1H, J=4.1 and 8.2 Hz); 7.16 (d, 2H, J=7.1 Hz); 6.83 (d, 2H, J=7.7 Hz); 3.86 (s, 3H) and 2.98 (m, 2H) ppm.

EXAMPLE 12

[1,8] naphthyridine-2-carboxylic acid (pyridin-3-ylmethyl)-amide Compound#12

$^1$NMR (300 MHz; CDCl$_3$): 9.13–9.12 (m, 1H); 8.79 (bs, 1H); 8.62 (bs, 1H); 8.49 (bs 1H); 8.39 (dd, 2H, J=8.2 and 15 Hz); 8.25 (dd, 1H, J=1.9 and 8.2 Hz); 7.70–7.69 (m, 1H); 7.54 (dd, 1H, J=4.4 and 8.2 Hz); 7.26–7.20 (m, 1H) and 4.68 (d, 2H, J=6.3 Hz) ppm.

EXAMPLE 13

[1,8] naphthyridine-2-carboxylic acid (pyridin-2-ylmethyl)-amide Compound#13

$^1$H NMR (300 MHz; CDCl$_3$): 9.21 (dd, 1H, J=1.9 and 4.2 Hz); 9.12 (bs, 1H); 8.61 (d, 1H, J=4.9 Hz); 8.49 (d, 1H, J=8.2 Hz); 8.41 (d, 1H, J=8.5 Hz); 8.30 (dd, 1H, J=1.9 and 8.2 Hz); 7.70–7.64 (m, 2H); 7.60 (dd, 1H, J=4.1 and 8.1 Hz); 7.38 (d, 1H, J=7.7 Hz); 7.26–7.20 (m, 1H) and 4.88 (d, 2H, J=6 Hz) ppm.

EXAMPLE 14

[1,8] naphthyridine-2-carboxylic acid pyridin-4-ylamide Compound#14

$^1$H NMR (300 MHz; CDCl$_3$): 10.45 (bs, 1H); 9.27 (dd, 1H, J=1.9 and 4.3 Hz); 8.65 (bs, 1H); 8.52 (dd, 2H, J=8.5 and 15 Hz); 8.36 (dd, 1H, J=1.9 and 8.2 Hz); 7.86 (m, 2H); 7.68 (dd, 1H, J=4.1 and 8.2 Hz) and 7.27–7.26 (m, 1H) ppm.

EXAMPLE 15

[1,8] naphthyridine-2-carboxylic acid pyridin-2-ylamide Compound#15

$^1$H NMR (300 MHz; CDCl$_3$): 10.77 (bs, 1H); 9.23 (bs, 1H); 8.52–8.28 (m, 5H); 7.79–7.74 (m, 1H); 7.63–7.59 (m, 1H) and 7.10–7.06 (m, 1H) ppm.

EXAMPLE 16

[1,8] naphthyridine-2-carboxylic acid 2-fluoro-benzylamide Compound#16

$^1$H NMR (300 MHz; CDCl$_3$): 9.14 (bs, 1H); 8.69 (m, 1H); 8.43 (d, 1H, J=8.5 Hz); 8.35 (d, 1H, J=8.5 Hz); 8.25 (dd, 1H, J=1.9 and 8 Hz); 7.55 (dd, 1H, J=4.1 and 8.1 Hz); 7.44–7.38 (m, 1H); 7.27–7.19 (m, 1H); 7.10–6.99 (m, 2H) and 4.74 (d, 2H, J=6 Hz) ppm.

EXAMPLE 17

[1,8] naphthyridine-2-carboxylic acid 2-chloro-benzylamide Compound#17

$^1$H NMR (300 MHz; CDCl$_3$): 9.13 (d, 1H, J=1.9 Hz); 8.73 (bs, 1H); 8.42 (d, 1H, J=8.5 Hz); 8.33 (d, 1H, J=8.5 Hz); 8.23

(dd, 1H, J =1.9 and 8.3 Hz); 7.53 (dd, 1H, J=4.1 and 8.2 Hz); 7.45–7.42 (m, 1H); 7.35–7.32 (m, 1H); 7.21–7.17 (m, 1H) and 4.77 (d, 2H, J=6 Hz) ppm.

EXAMPLE 18

[1,8] naphthyridine-2-carboxylic acid 2-trifluoromethoxy-benzylamide Compound#18

$^1$H NMR (300 MHz; CDCl$_3$): 9.16 (d, 1H, J=2.5 Hz); 8.7 (bs, 1H); 8.46 (d, 1H, J=8.2 Hz); 8.38 (d, 1H, J=8.5 Hz); 8.27 (dd, 1H, J=1.9 and 8.1 Hz); 7.57 (dd, 1H, J=4.1 and 8.2 Hz); 7.51–7.21 (m, 2H) and 4.78 (d, 2H, J=6 Hz) ppm.

EXAMPLE 19

[1,8] naphthyridine-2-carboxylic acid (3-nitrophenyl)-amide Compound#19

$^1$H NMR (300 MHz; CDCl$_3$): 9.25 (dd, 1H, J=1.9 and 4.1 Hz); 9.04 (t, 1H, J=1.9 Hz); 8.76 (d, 1H, J=8.5 Hz); 8.63 (dd, 1H, J=1.9 and 8.2 Hz); 8.40–8.35 (m, 2H); 8.02–7.99 (m, 1H); 7.79 (dd, 1H, J=4.1 and 8 Hz) and 7.69 (t, 1H, J=8.2 Hz) ppm.

EXAMPLE 20

N-(5,7-dimethyl-[1,8] naphthyridin-2-yl)-2-(2-methoxyphenyl)-acetamide Compound#20

$^1$H NMR (300 MHz; CDCl$_3$): 8.48 (d, 1H, J=8.8 Hz); 8.40 (bs, 1H); 8.27 (d, 1H, J=9 Hz); 7.35–7.28 (m, 2H); 7.08 (d, 1H, J=0.6 Hz); 7.00–6.93 (m, 2H); 3.90 (s, 3H); 3.80 (s, 2H); 2.66 (s, 3H) and 2.62 (s, 3H) ppm.

EXAMPLE 21

[1,8] naphthyridin-2-carboxylic acid benzyloxyamide Compound#21

$^1$H NMR (300 MHz; CDCl$_3$): 10.53 (bs, 1H); 9.18 (bs, 1H); 8.42 (m, 2H); 8.29 (d, 1H, J=7.1 Hz); 7.60 (m, 1H); 7.47–7.26 (m, 6H) and 5.1 (s, 2H) ppm.

EXAMPLE 22

[1,8] naphthyridine-2-carboxylic acid thiazol-2-ylamide Compound#22

$^1$H NMR (400 MHz; CDCl$_3$): 11.50 (bs, 1H); 9.25 (dd, 1H, J=1.8 and 4.1 Hz); 8.49 (dd, 2H, J=8.3 and 14 Hz); 8.33 (dd, 1H, J=1.8 and 8.2 Hz); 7.64 (dd, 1H, J=4.1 and 8.2 Hz); 7.58 (d, 1H, 3.5 Hz) and 7.07 (d, 1H, J=3.5 Hz) ppm.

EXAMPLE 23

[1,8] naphthyridine-2-carboxylic acid benzothiazol-2-ylamide Compound#23

$^1$H NMR (300 MHz; CDCl$_3$): 9.28 (d, 1H, J=4.1 Hz); 8.55–8.48 (m, 2H); 8.36–8.32 (m, 1H); 7.87 (d, 2H, J=8 Hz); 7.69–7.63 (m, 1H); 7.50–7.45 (m, 1H); 7.37–7.34 (m, 1H) and 7.32–7.26 (m, 1H) ppm.

EXAMPLE 24

[1,8] naphthyridine-2-carboxylic acid (2-fluoro-phenyl)-amide Compound#24

$^1$H NMR (300 MHz; CDCl$_3$): 10.4 (bs, 1H); 9.20 (dd, 1H, J=1.9 and 4.1 Hz); 8.51–8.39 (m, 3H); 8.27 (dd, 1H, J=1.8 8.2 Hz); 7.57 (dd, 1H. J=4.2 and 8.2 ) and 7.19–7.07 (m, 3H) ppm.

EXAMPLE 25

[1,8] naphthyridin-2-carboxylic acid (2-methoxy-benzyl)-methyl-amide Compound#25

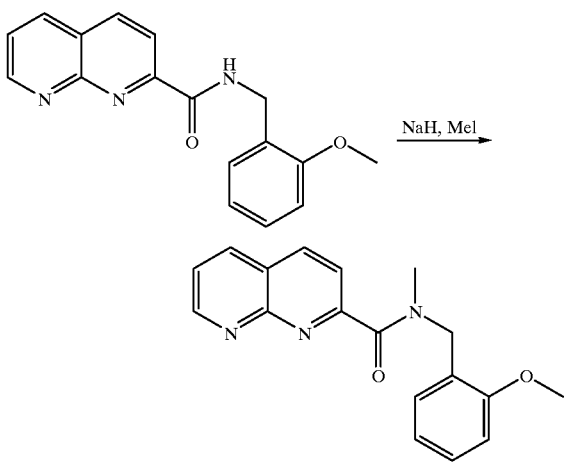

To a suspension of sodium hydride (10 mg) in DMF (1 mL) at 0° C. was added a solution of the compound of Example 1 (68 mg, 0.23 mmol) in DMF (1mL). The reaction mixture was stirred at the same temperature for 30 minutes then methyl iodide (20 μL, 0.32 mmol) was added. Reaction mixture was stirred at room temperature overnight. It was then poured into ethyl acetate, washed with water, brine, dried over magnesium sulfate and concentrated to give a white solid. Purification was done using a silica gel column and ethyl acetate as the eluent. $^1$H NMR (300 MHz; CDCl$_3$): Mixture of rotamers 9.13 (m, 1H); 8.29–8.18 (m, 2H); 7.86 (dd, 1H, J=8.2 and 12 Hz); 7.58–7.11 (complex mixture; 3H); 6.98–6.71 (complex mixture, 2H); 4.91 and 4.85 (2s, 2H) and 3.84 and 3.58 (2 s, 3H); 3.18 and 3.04 (2 s, 3H) ppm.

EXAMPLE 26

[1,8] naphthyridine-2-carbothioic acid 2-methoxy-benzylamide Compound#26

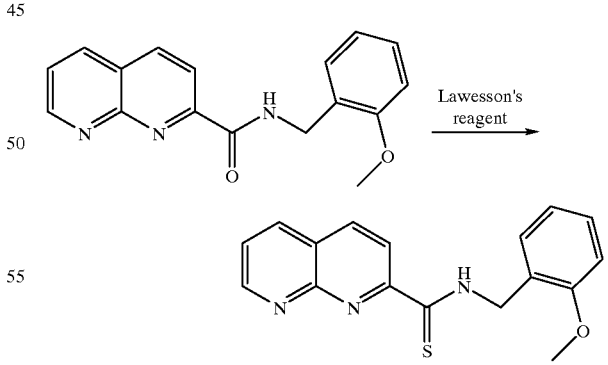

Lawesson's reagent (52 mg 0.13 mmol, 0.5 eq.) was added to a solution of the amide (75.3 mg, 0.26 mmol) in benzene (5 mL) and the solution was refluxed during 2 hours. Solvent was evaporated and the yellow solid was purified by flash chromatography using ethyl acetate/hexane 50% to give a yellow solid, which was precipitated with ether (62% yield).

$^1$H NMR (300 MHz; CDCl$_3$): 10.64 (bs, 1H); 9.15 (dd, 1H, J=1.9 and 4.1); 9.02 (d, 1H, J=8.5 Hz); 8.32 (d, 1H, J=8.5 Hz); 8.26 (dd, 1H, J=1.9 and 8.1 Hz); 7.56 (dd, 1H, J=4.1 and 8.2 Hz); 7.40 (dd, 1H, J=1.1 and 7.4 Hz); 7.33–7.26 (m, 1H); 6.95–6.90 (m, 2H); 5.10 (d, 2H, J=5.5 Hz) and 3.88 (s, 3H) ppm.

EXAMPLE 27

N-(2-methoxy-benzyl)-[1,8]naphthyridine-2-carboxamide trifluoroacetate Compound#27

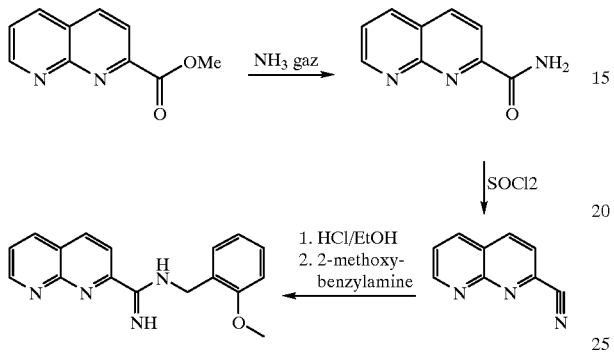

Ammonia was bubbled into a solution of the ester (144 mg, 0.76 mmol) in methanol (10 mL) at 0° C., until saturation of the solution. Then solution was closed and stirred at room temperature overnight. Reaction mixture was flushed with nitrogen and concentrated to give a white solid (100% yield). $^1$H NMR (300 MHz; CDCl$_3$): 9.17 (bs, 1H); 8.62 (d, 1H, J=8.2 Hz); 8.55 (dd, 1H, J=1.6 and 8.2 Hz); 8.35 (d, 1H, J=8.2 Hz); 7.74 (dd, 1H, J=4.3 and 8.2 Hz) and 4.87 (s, 2H) ppm.

Thionyl chloride (78 µL, 1.06 mmol, 1.4 eq.) was added to a solution of the amide (132 mg, 0.76 mmol) and NMM (0.24 mL, 2.128 mmol, 2.8 eq.) in DMF (8 mL) at 0° C. Reaction mixture was stirred at the same temperature for 30 minutes then at room temperature for 2 hours then it was poured into ice-cold water and extracted with ethyl acetate (3X). Combined extracts were washed with citric acid 10%, sodium bicarbonate saturated solution, brine, dried over magnesium sulfate and concentrated to give a green solid. Product was purified by flash chromatography using ethyl acetate to give a white solid (25% yield). $^1$H NMR (300 MHz; CDCl$_3$): 9.28 (dd, 1H, J=1.9 and 4.1 Hz); 8.42 (d, 1H, J=8.2 Hz); 8.32 (dd, 1H, J=1.9 and 8.2 Hz); 7.83 (d, 1H, J=8.2 Hz) and 7.66 (dd, 1H, J=4.1 and 8.3 Hz) ppm.

HCl gas was bubbled into a solution of the cyano compound (30 mg, 0.19 mmol) in ethanol (5 mL) at 0° C. (10 minutes). Reaction mixture was capped and put in the refrigerator for 18 hours. Then nitrogen was bubbled into the solution and the reaction mixture was concentrated. The residue was put into DMF (2 mL) and treated with triethylamine (26 µL, 0.19 mmol, 1eq.) and the amine (50 µL, 0.38 mmol, 2 eq.). Reaction mixture was stirred at 60° C. overnight. After cooling, the reaction mixture was partitioned between ethyl acetate and water. Organic layer was washed with water, brine, dried and concentrated to give a yellow oil.

Purification by flash chromatography using EtOAc/MeOH/NH$_4$OH 98/1/1 followed by an HPLC purification gave a white solid (98.6% pure) (25% yield). $^1$H NMR (300 MHz; CDCl$_3$): 9.14 (dd, 1H, J=1.9 and 4.4 Hz); 8.64 (d, 1H, J=8.5 Hz); 8.29–8.24 (m, 2H); 7.54 (dd, 1H, J=4.4 and 8 Hz); 7.29–7.21 (m, 1H); 6.98–6.89 (m, 2H); 4.56 (s, 2H); 3.83 (s, 3H); 3.84 (s, 1H) and 3.74 (s, 1H) ppm.

The following compounds were purchased at Peakdale:

[1,8] naphthyridine-2-carboxylic acid phenyl-amide Compound#28 (PFC 023)

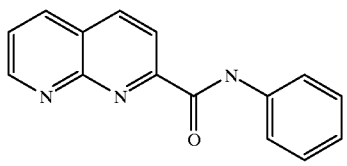

[1,8] naphthyridine-2-carboxylic acid pyridin-3-yl-amide Compound#29 (PFC-024)

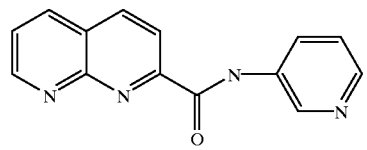

[1,8] naphthyridine-2-carboxylic acid (phenyl-3-trifluoromethyl)-amide Compound#30 (PFC-025)

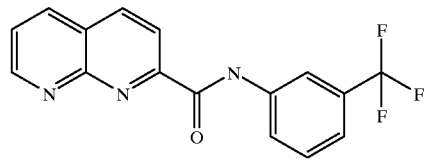

[1,8] naphthyridine-2-carboxylic acid (phenylmethyl-3-trifluoromethyl)-amide Compound#31 (PFC-026)

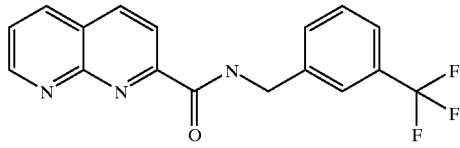

TABLE 1

COMPOUNDS OF THE PRESENT INVENTION

| compound # | Structure |
|---|---|
| 1 | 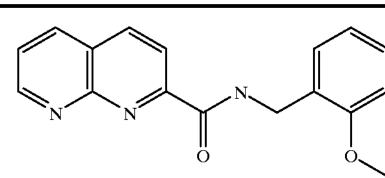 |

TABLE 1-continued

COMPOUNDS OF THE PRESENT INVENTION

| compound # | Structure |
|---|---|
| 2 | 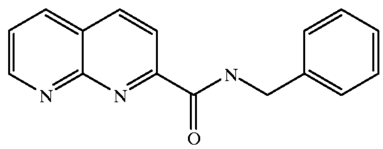 |
| 3 | 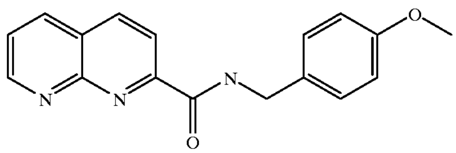 |
| 4 | 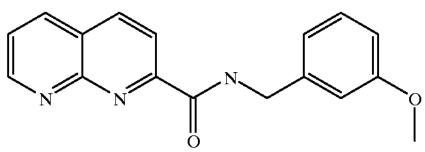 |
| 5 | 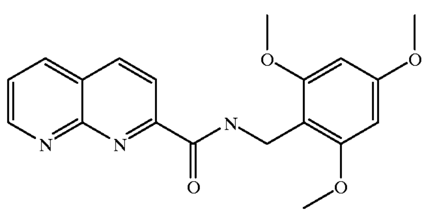 |
| 6 | 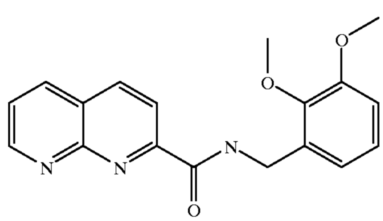 |
| 7 | 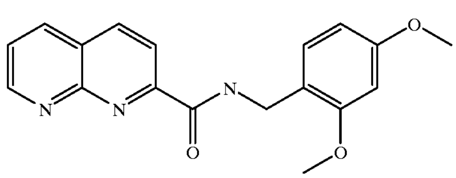 |
| 8 | 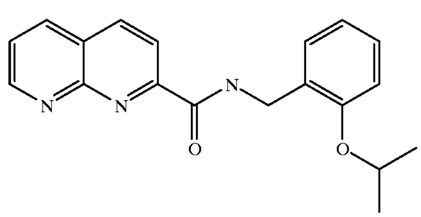 |
| 9 | |
| 10 | |
| 11 | |
| 12 | |
| 13 | |
| 14 | |
| 15 | |

TABLE 1-continued
COMPOUNDS OF THE PRESENT INVENTION
| compound # | Structure |
|---|---|
| 16 | 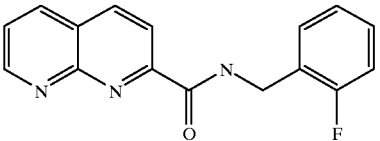 |
| 17 | 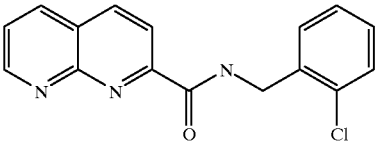 |
| 18 | 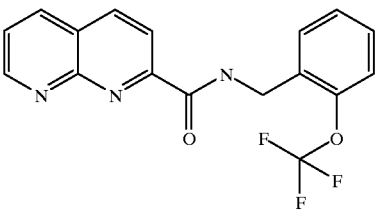 |
| 19 | 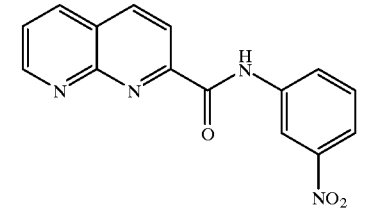 |
| 20 | 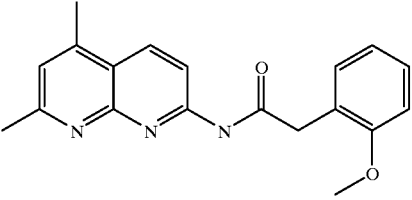 |
| 21 | 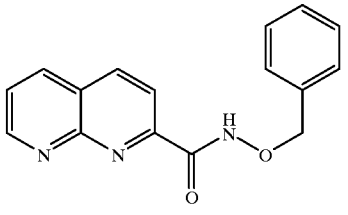 |
| 22 | 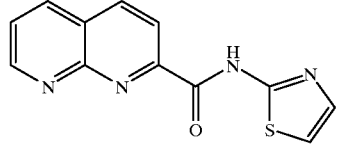 |
| 23 | 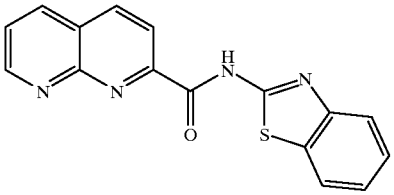 |
| 24 | 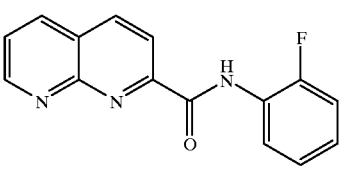 |
| 25 | 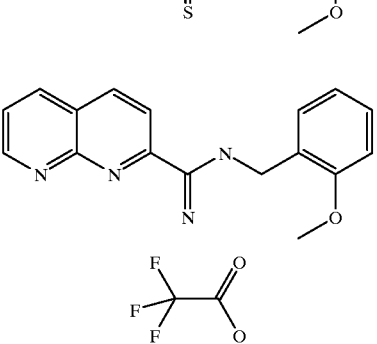 |
| 26 | 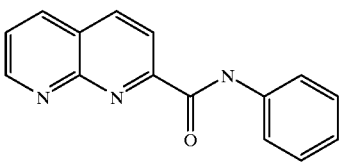 |
| 27 | 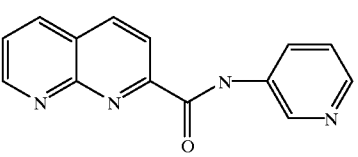 |
| 28 | |
| 29 | |

TABLE 1-continued

COMPOUNDS OF THE PRESENT INVENTION

| compound # | Structure |
|---|---|
| 30 | (1,8-naphthyridine-2-carboxamide with N-[3-(trifluoromethyl)phenyl]) |
| 31 | (1,8-naphthyridine-2-carboxamide with N-CH2-[3-(trifluoromethyl)phenyl]) |

EXAMPLE 28

ANTIVIRAL ACTIVITY

BVDV Anti-Viral Assay

Currently, the WST-1 based BVDV assay, is being used as surrogate to evaluate potential anti-HCV agents since BVDV (bovine viral diarrhea virus) shares functional homology with the HCV.

WST-1 Based BVDV Anti-Viral Assay

To determine the anti-viral effect of the compounds, MDBK cells were infected with the cytopathic strain of BVDV(NADL) using a 0.006 to 0.01 MOI. 3000 cells were then seeded in each well of a 96-well plate containing the compound. The final volume was 200 μl of media per wells. Following 4 days incubation at 37° C., medium was removed and 100 μl of WST-1 (diluted 1/40) in culture media was added to wells. Cell culture was then incubated for another 2 hrs at 37° C., after which 20 μl of 10% SDS was added to each well in order to inactivate the virus and the OD at 450 nm was determined using a microplate reader (Dynatech MR5000).

In parallel, the same experiment was performed using non-infected cells to determine the compound toxicity. The percentage of cytopathic effect (CPE) reduction and the percentage of viable cells is calculated using these data. The results appear in Table 2 below.

| compound # | BVDV antiviral effect $IC_{50}$ (μM) | Toxicity WST-1 $CC_{50}$ (μM) |
|---|---|---|
| 1 | ~6.8 | >68.2 |
| 2 | <76 | >76 |
| 3 | ~1.7 | >68.2 |
| 4 | ~6.8 | >68.2 |
| 5 | ~1.1 | >56.6 |
| 8 | <62.2 | >62.2 |
| 10 | >6 | >6 |
| 12 | ~18.9 | >75.7 |
| 13 | >7.6 <75.7 | >75.7 |
| 15 | >8 | >79.9 |
| 16 | ~1.1 | >71.1 |
| 17 | ~3.6 | >67.2 |
| 19 | ~1.7 | >68 |
| 22 | >0.78 <7.8 | >78 |
| 23 | >0.65 <6.5 | >6.5 |
| 24 | ~7.5 | >74.8 |
| 27 | ~0.33 | >63.2 |
| 28 | >8 <80 | >80.2 |
| 29 (HCl salt) | ~3.2 | >79.9 |
| 30 | ~0.6 | 6.3 |
| 31 | ~3 | >60.4 |

HERPES SIMPLEX VIRUS PLAQUE REDUCTION ASSAY

Confluent monolayers of Vero cells in 24-well tissue culture dishes were inoculated with 300 μl of HSV-1 (300 pfu/ml) (KOS) or HSV-2 (300 pfu/ml)(186) diluted in PMEM medium. After adsorption at 37° C. for one hour the monolayers were overlaid with medium containing test compound at several concentrations. Infected but otherwise untreated monolayers were included in the assay as virus controls. After incubation at 37° C. in 5% $CO_2$/air post-infection for 48 hours, the plates were fixed and stained with crystal violet 2%/EtOH 20% for a few seconds. The monolayers were examined for the presence of plaques under a microscope. The percentage plaque reduction was determined for each compound and the 50% inhibitory concentration ($IC_{50}$) established.

The $CC_{50}$ value (cell cytotoxicity dose at 50%) was assessed on virus-free control layers of cells to assess the toxicity of the compounds.

Inhibition of Human Hepatitis B Virus.

The method used for this test is described in detail in Korba et al., Antiviral Research 15, 217–228 (1992) which is shortly described as follows:

Hep G2 cells transfected with human hepatitis B virus genomic DNA (2.2.15 cells) were grown and maintained in RPMI-1640 culture medium containing %5 foetal bovine serum. 2 mM glutamine and 50 μg/ml gentamicin sulphate, and checked routinely for G418 resistance. Cultures of 2.2.15 cells were grown to confluence in 24 well tissue culture plates and maintained for 2 to 3 days in that condition prior to drug treatment.

Drugs were dissolved in sterile water or sterile 50% DMSO in water at concentrations 100-fold higher than the higher test concentration. These solutions were diluted as needed in culture medium.

The culture medium on the confluent cells was changed 24 hours prior to exposure to test compounds. During the 10 day treatment, the culture medium was changed daily. After 10 days of the treatment, the culture medium was collected and frozen at −70° C. for HBV DNA analysis.

To analyse extracellular HBV DNA, 0.2 ml samples of culture medium were incubated for 20 minutes at 25° C. in 1M NaOH/10X SSC (1X SSC is 0.15M NaCl/0.015M Sodium Citrate, pH 7.2) and then applied to nitrocellulose membranes presoaked in 20X SSC. Filters were then rinsed in 2X SSC and baked at 80° C. for 1 hour under vacuum.

A purified 3.2 kb EcoR1 HBV DNA fragment was labelled with [$^{32}$P]dCTP by nick translation and used as a probe to detect HBV DNA on the dot-blot by DNA hybridisation. After washing, the hybridised blot was dried and $^{32}$P was quantified using an Ambis beta scanner.

What is claimed is:

1. A method for the inhibition of a viral infection in a mammal, the method comprising administering to the mammal, an antiviral amount of a (1,8) naphthyridine derivative of Formula I or a pharmaceutically acceptable salt thereof;

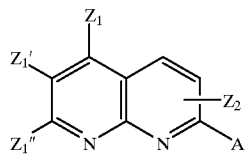

wherein $Z_1$, $Z_1'$, $Z_1''$, and $Z_2$ are independently H, halogen, carboxyl, amino, amidino, guanidino, nitro, OH, SH, CN, $C_{1-6}$ alkyl, $C_{2-6}$ alkenyl, $C_{2-6}$, alkynyl, $C_{1-6}$ alkoxy or $C_{1-6}$ heteroalkyl;

A is

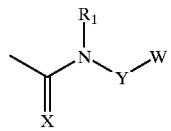

(III)

X is O, NH or S;

Y is O, S, $(CH_2)_n$, $O(CH_2)_n$, or $S(CH_2)_n$; with n is 0 to 6;

$R_1$ is independently H or $C_{1-6}$ alkyl, $C_{2-6}$ alkenyl, or $C_{2-6}$ alkynyl;

W is $C_{6-12}$ aryl, $C_{6-12}$ heteroaryl, or $C_{3-12}$ heterocycle.

2. The method of claim 1 wherein $Z_1$, $Z_1'$, $Z_1''$ and $Z_2$ are independently $C_{1-6}$ alkyl, $C_{2-6}$ alkenyl, $C_{2-6}$ alkynyl which can be substituted with one or more halogen, OH, carboxy, amino, guanidino, amidino, nitro, SH or CN.

3. The method of claim 1 wherein $R_1$ is independently $C_{1-6}$ alkyl, $C_{2-6}$ alkenyl, $C_{2-6}$ alkynyl which is substituted by one or more $C_{1-6}$ alkyl, $C_{1-6}$ alkoxy or $C_{1-6}$ alkylthio, halogen, amino, guanidino, amidino nitro, OH, SH or CN.

4. The method of claim 1 wherein W is $C_{6-12}$ aryl, $C_{6-12}$ heteroaryl, $C_{3-12}$ heterocycle, either of which is substituted by one or more $C_{1-6}$ alkyl, $C_{2-6}$ alkenyl, $C_{2-6}$ alkynyl, $C_{1-6}$ perfluoroalkyl, $C_{1-6}$ alkoxy, $C_{1-6}$ perfluoroalkoxy, $C_{1-6}$ heteroalkyl, $C_{1-6}$ perfluoroalkylthio, halogen, amino, guanidino, amidino, nitro, OH, COOH, SH or CN.

5. The method of claim 1 wherein Y is $(CH_2)_n$ and wherein n is chosen between 0 to 6.

6. The method of claim 1 wherein X is O.
7. The method of claim 1 wherein X is S.
8. The method of claim 1 wherein X is NH.
9. The method of claim 1 wherein $R_1$ is H.
10. The method of claim 1 wherein $Z_1$, $Z_1'$ and $Z_1''$ are H.
11. The method of claim 1 wherein $Z_2$ is H.

12. The method of claim 1 wherein $Z_1$, $Z_1'$, $Z_1''$ and $Z_2$ are H.

13. The method of claim 1 wherein $R_1$, $Z_1$, $Z_1'$, $Z_1''$ and $Z_2$ are H.

14. The method of claim 1 wherein $R_1$, $Z_1$, $Z_1'$, $Z_1''$ and $Z_2$ are H and Y is $(CH_2)_n$ wherein n is chosen between 0 to 6.

15. The method of claim 1 wherein n is 0.
16. The method of claim 1 wherein W is phenyl or pyridinyl unsubstituted or substituted with one or more $C_{1-6}$ alkoxy groups.

17. The method of claim 1 wherein $R_1$, is H, $Z_1$, $Z_1'$, $Z_1''$, are H and $Z_2$, is H.

18. The method of claim 1 wherein Y is $(CH_2)_n$ and n is 0.

19. The method of claim 1, wherein Y is $(CH_2)_n$ and n is 1.

20. The method of claim 1 wherein Y is $(CH_2)_n$ and n is 2.

21. The method of claim 1 wherein X is S, $R_1$ is H, $Z_1$, $Z_1'$, $Z_1''$, are H and $Z_2$, is H.

22. The method of claim 1 wherein X is O, $R_1$ is H, $Z_1$, $Z_1'$, $Z_1''$, are H and $Z_2$, is H.

23. The method of claim 1 wherein X is NH, $R_1$ is H, $Z_1$, $Z_1'$, $Z_1''$, are H and $Z_2$, is H.

24. The method according to claim 1 wherein said naphthyridine derivative is in the form of the (+) enantiomer, the (−) enantiomer or mixture of the (+) and (−) enantiomer including racemic mixture.

25. The method according to claim 1 wherein the viral infection is hepatitis or herpes.

26. The method according to claim 1 wherein the viral infection is HBV or HCV.

27. The method according to claim 1, wherein the viral infection is HCV.

28. The method according to claim 1, wherein the viral infection is HSV-1 or HSV-2.

29. The method according to claim 28 wherein the viral infection is HCV.

30. A method for the inhibition of a viral infection in a mammal, the method comprising administering to the mammal an antiviral amount of a [1,8] naphthyridine derivative selected from the group consisting of:

[1,8] naphthyridine-2-carboxylic acid 2-methoxybenzylamide (Compound #1);

[1,8] naphthyridine-2-carboxylic acid benzylamide (Compound #2);

[1,8] naphthyridine-2-carboxylic acid 4-methoxybenzylamide (Compound #3);

[1,8] naphthyridine-2-carboxylic acid 3-methoxybenzylamide (Compound #4);

[1,8] naphthyridine-2-carboxylic acid 2,4,6-trimethoxybenzylamide (Compound #5);

[1,8] naphthyridine-2-carboxylic acid 2,3-dimethoxybenzylamide (Compound #6); [1,8] naphthyridine-2-carboxylic acid 2,4-dimethoxy-benzylamide (Compound #7);

[1,8] naphthyridine-2-carboxylic acid 2-isopropoxybenzylamide (Compound #8);

[1,8] naphthyridine-2-carboxylic acid [2-(2-methoxyphenyl)ethyl]-amide (Compound #11);

[1,8] naphthyridine-2-carboxylic acid (pyridin-3-ylmethyl)-amide (Compound #12);

[1,8] naphthyridine-2-carboxylic acid (pyridin-2-ylmethyl)-amide (Compound #13);

[1,8] naphthyridine-2-carboxylic acid pyridin-4-ylamide (Compound #14);

[1,8] naphthyridine-2-carboxylic acid pyridin-2-ylamide (Compound #15);

[1,8] naphthyridine-2-carboxylic acid 2-fluoro-benzylamide (Compound #16);

[1,8] naphthyridine-2-carboxylic acid 2-chloro-benzylamide (Compound #17);

[1,8] naphthyridine-2-carboxylic acid 2-trifluoromethoxy-benzylamide (Compound #18);

[1,8] naphthyridine-2-carboxylic acid (3-nitrophenyl)-amide (Compound #19);

[1,8] naphthyridine-2-carboxylic acid benzyloxyamide (Compound #21);

[1,8] naphthyridine-2-carboxylic acid thiazol-2-ylamide (Compound #22);

[1,8] naphthyridine-2-carboxylic acid benzothiazol-2-ylamide (Compound #23);

[1,8] naphthyridine-2-carboxylic acid (2-fluoro-phenyl)-amide (Compound #24);

[1,8] naphthyridine-2-carboxylic acid (2-methoxy-benzyl)-methyl-amide (Compound #25);

[1,8] naphthyridine-2-carboxylic acid 2-methoxy-benzylamide (Compound #26);

(2-methoxy-benzyl)-[1,8] naphthyridine-2-carboxamidine trifluoroacetate (Compound #27);

[1,8] naphthyridine-2-carboxylic acid phenyl-amide (Compound #28);

[1,8] naphthyridine-2-carboxylic acid pyridin-3-yl-amide (Compound #29);

[1,8] naphthyridine-2-carboxylic acid (phenyl-3-trifluoromethyl)-amide (Compound #30); and

[1,8] naphthyridine-2-carboxylic acid (phenylmethyl-3-trifluoromethyl) (Compound #31).

31. The method according to claim 30 wherein said naphthyridine derivative is in the form of the (+) enantiomer, the (−) enantiomer or mixture of the (+) and (−) enantiomer including racemic mixture.

32. A method for the inhibition of a viral infection in a mammal, the method comprising administering to the mammal an antiviral amount of a [1,8] naphthyridine derivative selected from the group consisting of (+)-[1,8] naphthyridine-2-carboxylic acid 2-sec-butoxy-benzylamide (Compound #9); and (−)-[1,8] naphthyridine-2-carboxylic acid 2-sec-butoxy-benzylamide (Compound #10).

33. The method of claim 30 wherein said [1,8] naphthyridine derivative is selected from the group consisting of:

[1,8] naphthyridine-2-carboxylic acid 2-methoxybenzylamide (Compound #1);

[1,8] naphthyridine-2-carboxylic acid benzylamide (Compound #2);

[1,8] naphthyridine-2-carboxylic acid 4-methoxy-benzylamide (Compound #3);

[1,8] naphthyridine-2-carboxylic acid 3-methoxy-benzylamide (Compound #4);

[1,8] naphthyridine-2-carboxylic acid 2,4,6-trimethoxy-benzylamide (Compound #5);

[1,8] naphthyridine-2-carboxylic acid (pyridin-3-ylmethyl)-amide (Compound #12);

[1,8] naphthyridine-2-carboxylic acid 2-fluoro-benzylamide (Compound #16);

[1,8] naphthyridine-2-carboxylic acid 2-chloro-benzylamide (Compound #17); and (2-methoxy-benzyl)-[1,8]naphthyridine-2-carboxamidine trifluoroacetate (Compound #27).

34. The method according to claim 33 wherein said naphthyridine derivative is in the form of the (+) enantiomer, the (−) enantiomer or mixture of the (+) and (−) enantiomer including racemic mixture.

35. The method according to claim 30 wherein the viral infection is hepatitis or herpes.

36. The method according to claim 30 wherein the viral infection is HBV or HCV.

37. The method according to claim 30, wherein the viral infection is HCV.

38. The method according to claim 30, wherein the viral infection is HSV-1 or HSV-2.

39. A composition useful as an antiviral agent, the composition comprising at least one [1,8] naphthyridine derivative of Formula I or a pharmaceutically acceptable salt thereof;

(I)

wherein A, $Z_1$, $Z_1'$, $Z_1''$ and $Z_2$ are as defined in claim 1.

40. A composition useful as an antiviral agent, the composition comprising at least one [1,8] naphthyridine derivative of Formula I or a pharmaceutically acceptable salt thereof;

wherein A, $Z_1$, $Z_1'$, $Z_1''$ and $Z_2$ are as defined in claim 24.

41. The composition according to claim 40, wherein the antiviral activity is anti-hepatitis or anti-herpes.

42. The composition according to claim 40, wherein said is anti-hepatitis activity is anti-HBV or anti-HCV.

43. The composition according to claim 40, wherein said anti-hepatitis activity is anti-HCV.

44. The composition according to claim 40, wherein said anti-viral activity is anti-HCV.

45. The composition according to claim 40, wherein said anti-herpes activity is anti-HSV-1 or anti-HSV-2.

* * * * *